(12) United States Patent
Kolich

(10) Patent No.: US 6,290,658 B1
(45) Date of Patent: Sep. 18, 2001

(54) RUNNER MONITORING DEVICE

(76) Inventor: Mark S. Kolich, 4729 5th Ave., Beaver Falls, PA (US) 15010

( * ) Notice: Subject to any disclaimer, the term of this patent is extended or adjusted under 35 U.S.C. 154(b) by 0 days.

(21) Appl. No.: 09/425,913

(22) Filed: Oct. 25, 1999

(51) Int. Cl.[7] ........................................ A61B 5/00
(52) U.S. Cl. ................................................ 600/595
(58) Field of Search ........................ 600/587, 595; 2/410, 10

(56) References Cited

U.S. PATENT DOCUMENTS

| | | |
|---|---|---|
| 2,494,278 | 1/1950 | Badovinac . |
| 2,565,381 | 8/1951 | Leighton . |
| 3,673,696 | 7/1972 | Wasson . |
| 4,528,990 | 7/1985 | Knowles . |
| 4,789,159 | 12/1988 | Kane . |
| 5,158,089 * | 10/1992 | Sweezey et al. ............ 600/595 |
| 5,425,378 * | 6/1995 | Sweezey et al. ............ 600/595 |

* cited by examiner

*Primary Examiner*—Max Hindenburg
(74) *Attorney, Agent, or Firm*—George C. Atwell

(57) ABSTRACT

A device for continuously monitoring the orientation of an individual's physical posture relative to a path the individual is traversing includes a transparent tube attachable to the bill of the individual's cap, and extending beneath and to opposed sides of the bill, a pair of fastening elements with each fastening element securable to an end of the tube so that the tube can be secured to the bill by the fastening elements, and a spherical member disposed and visible within the bore of the tube and susceptible to shifting therein as a result of the individual's movement while traversing the path.

2 Claims, 2 Drawing Sheets

RUNNER MONITORING DEVICE

FIELD OF THE INVENTION

The present invention pertains to a physical movement monitoring device and, more particularly, pertains to a device for continuously monitoring the orientation of the physical posture of an individual while traversing a predetermined trail, track or path.

The physical health, fitness, and well-being movement of the past four decades has created a vast industry of products and publications dedicated to the maintenance, measurement, improvement, and enhancement of an individual's physical attributes and abilities, such as strength, stamina, quickness, agility, speed, good muscle tone, substantial lung capacity, and a sound cardiovascular system. Health and fitness publications covering subjects from aerobics to white water rafting, power weight lifting to line dancing, describe and advertise an enormous variety of items that allow an individual to gauge, monitor, improve, and refine physical performance and ability.

Although the physical activities of walking and running, whether pursued as an avocation or as a sport, may not ostensibly appear to lend themselves to the use of gadgetry and scientific instrumentation and measurement, a perusal of any publication devoted to walking and running demonstrates otherwise.

For any serious walker or runner, one of the most critical factors in obtaining maximum results from the workout or training session, and for avoiding injury, is maintaining proper body form or posture, with an emphasis on the proper posture for the torso and head. For walkers and runners, the correct form or body posture includes the eyes forward and the head and neck erect but relaxed. The shoulders should be relaxed but upright, and the back should be straight and upright with the lower back slightly curved. The hands should be held in relaxed fists, and the arms should be bent approximately 90° with the elbows held close to the body for smooth back-and-forth swinging to assist in propelling the body forward. In addition, the legs should be lifting forward from the hips, and the legs should be pushing off from the front portion of the feet.

Both runners and walkers encounter a number of problems and mistakes in attempting to maintain correct form or body posture. For example, many walkers and runners hold the head too far forward with respect to the axis of the torso. The human head weighs between eight and twelve pounds and, if it extends too far forward, this poor posture creates extra work and additional strain for the muscles of the neck, back, and shoulders. In addition, indiscriminately flapping or swinging arms, stomping feet and oversized strides are clear indications of poor body posture. Measured steps and controlled and rhythmic arm swinging rectify these mistakes.

Yet another problem related to posture is that both walkers and runners may develop the habit of dipping one or both of their shoulders as a lengthened and strenuous walk or run increases muscle strain and fatigue. One consequence of the dipping of the shoulders is that the walker or runner's entire body tends to lean or list to one side, or, alternatively, from side to side, and, thus, his or her stride or pace becomes erratic and uneven. As a result of this erratic and uneven movement, there is a marked increase in muscle strain and fatigue not only in the neck, back, and shoulders, but also through the hips, thighs, and calves. Also, undue stress is applied to the foot on the listing or leaning side. Moreover, the dipping of one or both shoulders invariably causes the walker or runner to lean too far forward from the waist up thereby completely thwarting the effort to maintain the proper erect and upright posture that eases and enhances any walking or running workout or training session. Thus, the walker or runner's physical posture or form, embodying, among other attributes, his gait, pace, and stride, is undermined and ruined when the individual lapses into any of the above-described bad habits.

DESCRIPTION OF THE PRIOR ART

In order to obviate and rectify such inimical habits as holding the head too far forward, dipping one or both shoulders which thereby causes the entire body to lean or list to one side, and also bending and leaning too far forward from the waist up, the prior art discloses a number of devices for indicating and measuring the position and angular movement of the human body so that proper body posture can be maintained.

U.S. Pat. No. 2,494,278 (Badovinac) discloses a housing mountable to the brim of a hat. The housing encases a roller that rolls forward as the person's head or body tilts forward and rearward as the head returns to the upright position.

U.S. Pat. No. 2,565,381 (Leighton) discloses a device for measuring angular body movements and which is strapped to the body part or appendage for which measurement is desired. The device includes a calibrated dial and a pointer, both of which are freely and independently rotatable to register the amount of angular flexion in a body part or appendage.

U.S. Pat. No. 4,789,159 (Kane) discloses a device for assisting a golfer in maintaining his visual line of sight with the golf ball during the golfer's swing. The device includes a pair of frame members which connect together and seat on the golfer's head like glasses. The frame members include a chamber substantially filled with a liquid but including an air bubble. The golfer maintains a level line of sight with the golf ball by keeping the air bubble in the center of the chamber throughout the golfer's swing.

None of the above devices, however, are useful for walkers or runners that need to maintain proper body posture and an even, fluid gait or pace throughout their workout or training session.

SUMMARY OF THE INVENTION

The present invention comprehends a body posture monitoring device and, more particularly, comprehends a device for monitoring the orientation of a walker's or runner's body posture and form relative to a traversed path.

The device for monitoring the walker's or runner's body posture and form is removably attachable to the bill of a cap and extends beneath the bill and in front of the individual so the device is continuously viewable by the individual.

The device includes an elongated, transparent tube having a first end, an opposite second end, and an internal bore coequal in length with the tube. The tube can be arcuate-shaped throughout its length, or the tube can be bendable in order to form the arcuate shape for attachment to the bill of the cap. Disposed within the tube, for free, unimpeded, reciprocable movement therein is a shiftable means which is continuously discernible to the individual for providing immediate and constant feedback to the individual on the orientation of the individual's body posture relative to the traversed path and any lateral deviation from the proper upright body posture while traversing the path during the exercise or training session. The shiftable means may be a spherical member, such as a ball bearing, a pellet, or a BB, disposed within the interior bore. The back-and-forth movement of the spherical member occurs concomitant with the movement of the individual on the path so that the spherical member is seen by, and immediately indicates to, the individual any deviations from proper body posture, as well as when proper body posture and form are being maintained.

The tube is preferably attached to opposite sides of the bill of the cap adjacent the area where the bill connects or merges to the cap, and each fastening element includes a plug for insertion into the interior bore at the first and second end so that the bore can be sealed for retaining therein the spherical member.

It is an objective of the present invention to provide a monitoring device which provides immediate and continuous feedback to the individual of the orientation of the individual's body posture relative to a traversed path.

It is another objective of the present invention to provide a monitoring device which gives the walker or runner an eye-level focus point.

It is still another objective of the present invention to provide a monitoring device which gives the walker or runner an object or element to mentally concentrate upon in order to supplant the individual's awareness of his or her fatigue and pain.

It is yet another objective of the present invention to provide a monitoring device which gives immediate and continuous feedback to the individual of the individual's posture and form in order for the individual to maintain the correct upright body posture and form throughout an exercise session.

A further objective of the present invention is to provide a monitoring device which gives immediate feedback if a walker or runner lists to one side so that the incorrect body posture can be promptly corrected and brought back to the proper upright position relative to the traversed path.

A still further objective of the present invention is to provide a monitoring device that is viewable at nighttime and in all weather conditions.

Yet another objective of the present invention is to provide a monitoring device which can be used in rehabilitation and physical therapy settings for assisting the injured individual in gradually attaining, as much as possible, the correct and upright body posture.

These and other objects, features and characteristics of the present invention may be better understood from the following detailed description of the preferred embodiment when read in conjunction with the appended drawing figures.

DETAILED DESCRIPTION OF THE PREFERRED EMBODIMENT

Illustrated in FIGS. 1–6 is a monitoring device 10 which allows an individual 12, such as a walker or runner, to continuously monitor the orientation of his or her physical posture and form while traversing, or moving over, a predetermined path, surface, trail, track, or ground. The device 10 of the present invention is lightweight, durable, and easily carried or stored in a gym bag, purse, or gym locker. The device 10 provides continuous and immediate feedback to the individual 12 so that the individual 12 is continuously cognizant of his or her body posture while walking and running; as well as an deviations or lapses, especially lateral deviations, from the desired upright and vertical body posture relative to the traversed path.

Figure 1:
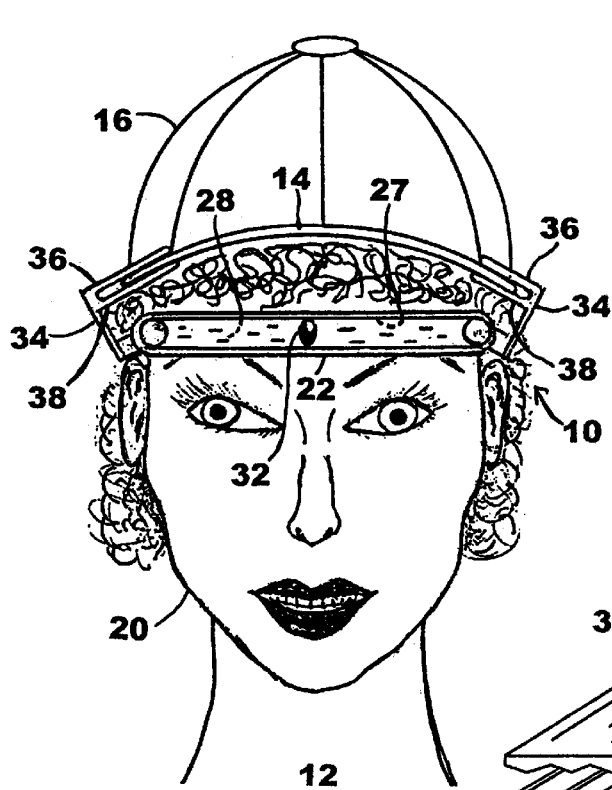
FIG. 1 is a front elevational view of the device of the present invention.
Figure 4:
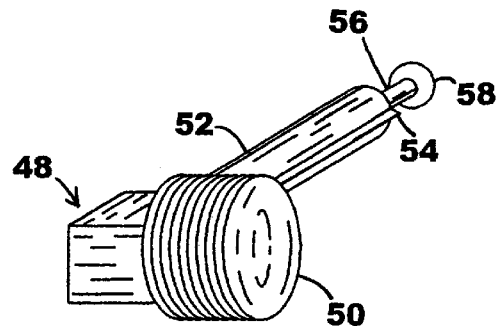
FIG. 4 is an enlarged perspective view of element of the device first shown in FIG. 3.
Figure 3:
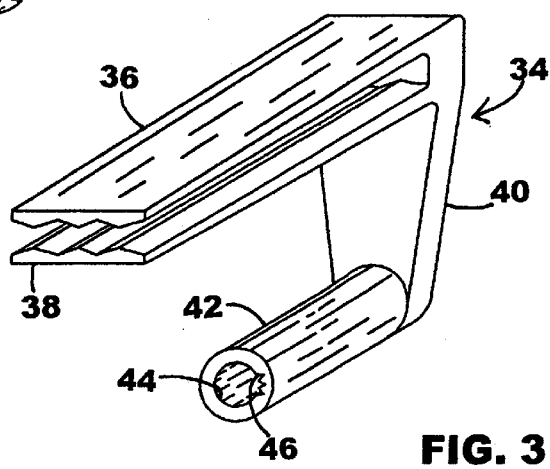
FIG. 3 is an enlarged perspective view of elements of the device first shown in FIG. 1.
Figure 5:
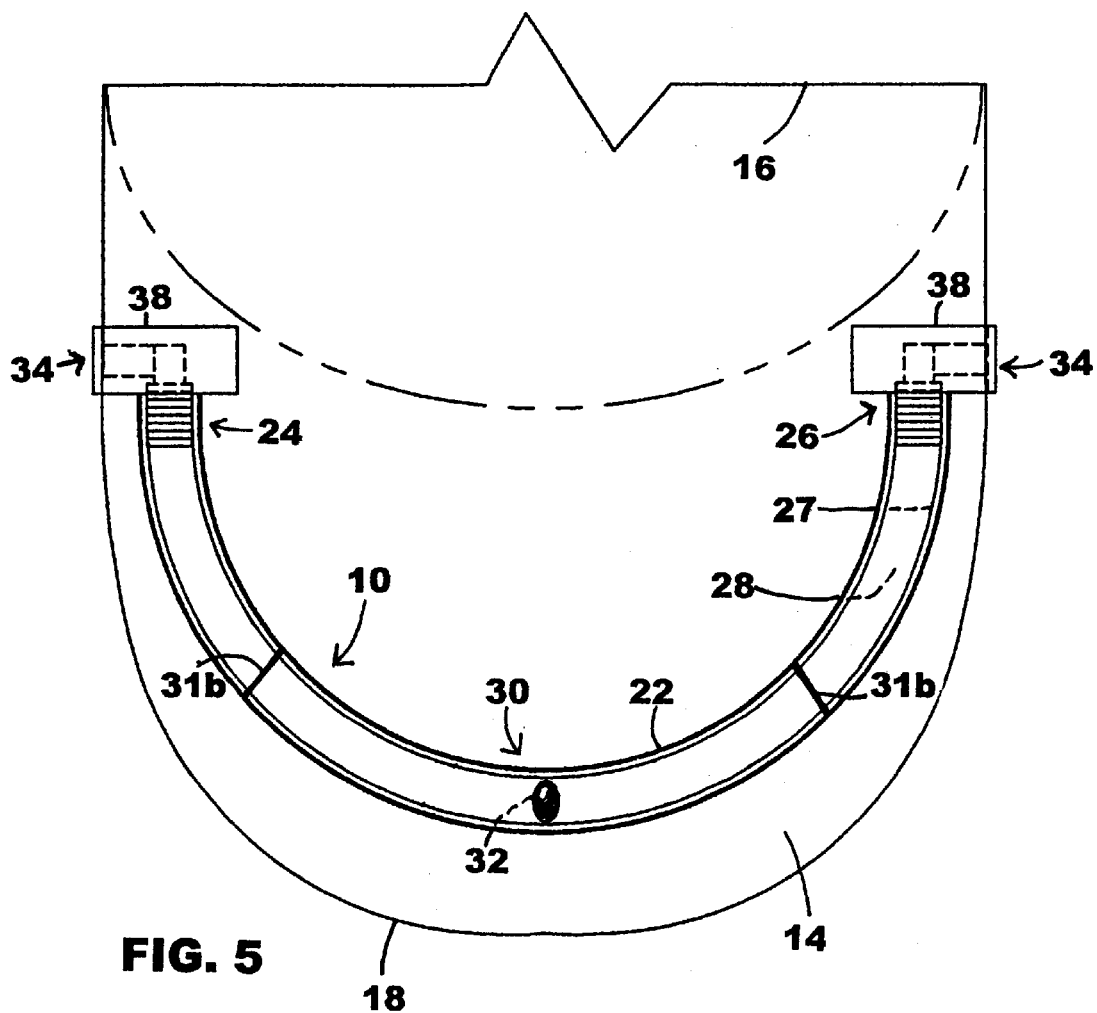
FIG. 5 is a bottom plan view of the device first shown in FIG. 1.

As shown in FIGS. 1 and 5, the device 10 is removably securable to the brim or bill 14 of a cap 16. The bill 14 comprises a generally half-circle or semicircular main body portion having a forward midpoint and opposed upper and lower surfaces. The bill 14 merges with or attaches to the cap 16 along one long, inner arcuate edge with the remainder of the bill 14 defined by an outer, continuous, arcuate peripheral edge 18. The part of the bill 14 that merges with or attaches to the cap 16 also defines the furthermost opposed sides of the bill 14. The device 10 is designed to be removably attachable to the opposite sides of the bill 14 so that the device 10 will extend beneath the bill 14 and immediately in front of the individual 12 in order that the device 10 is always positioned on the head 20 of the individual 12 at eye level or slightly above eye level.

As illustrated in FIGS. 1–6, the device 10 includes an elongated, bendable, transparent tube 22 (for example, composed of polyurethane or TEFLON) which extends in its operative position beneath the bill 14 and is capable of removable attachment to the opposite sides of the bill 14. The tube 22 is generally arcuate throughout its length and further includes a first end 24, an opposite second end 26, and an interior annular sidewall 27 coextensive with an internal chamber, passageway or bore 28. The bore 28 is coequal in length with the tube 22, and the tube 22 can be sized so that it extends beneath the bills of both children's and adult-sized caps. In addition, the tube 22 defines a central point or midpoint 30 when disposed in its operative position which is that part of the tube 22 located equidistant from both ends 24 and 26.

In order to provide a continuously viewable means by which body posture and physical performance can be continuously monitored by the individual 12, a shiftable means is disposed within the bore 28 of the tube 22. The shiftable means is gravity responsive to allow the individual 12 to continuously monitor body posture, form, and stride by simply observing the position and movement of the shiftable means within the bore 28. The shiftable means is capable of unimpeded, back-and-forth movement within the bore 28 from the first end 24 to the second end 26 so that the movement of the shiftable means occurs concomitant with the particular movement of the individual 12 on the path during a walking or running workout or training session. For example, if the individual 12 is running on a track and begins to lean or list toward the inside of the track, the shiftable means will move, roll, or shift within the tube 22 toward the respective end 24 or 26 that is angled downward as a result of the individual's torso and head 20 leaning to the inside of the track. If the individual 12 continues to lean to the inside of the track, the shiftable means will remain in that position within the bore 28.

If the individual 12 should start to lean to the outside of the track, the shiftable means will move toward the end 24 or 26 that is angled or pointing down toward the outside of the track as a result of this tilting or lateral deviation from the correct upright body posture. As soon as the individual 12 views this movement of the shiftable means within the tube 22, he is immediately aware that his body posture has again deviated from the proper form, and, to regain the proper form, the shiftable means must be returned to the area of the midpoint 30.

By observing the movement of the shiftable means within the bore 28, the individual 12 is made immediately aware that a lateral deviation from the generally upright and vertical body posture relative to the track has occurred. The individual 12 can then correct this deviation from the proper posture by righting himself with respect to the track, and, as he does, the shiftable means will move from the end 24 or 26 that was angled downward to a central zone, region, or area about the midpoint 30 of the tube 22. The midpoint 30 is further defined by a visible marking means that includes a center line 31a which encircles the tube exterior and may be painted or taped thereon. Furthermore, when the individual 12 views the shiftable means within the central region which is further defined by at least one pair of reference marks 31b, also painted or taped thereon to encircle the exterior sidewall of the tube 22, and equidistant from the center line 31a, the individual 12 immediately knows that he has returned his posture to a generally upright and vertical disposition with respect to the track. The shiftable means should remain within the region defined by the reference marks 31b as long as the upright posture is maintained. It should be noted that the shiftable means will not actually stay at the exact midpoint 30 but will slightly shift or jostle back-and-forth around the midpoint 30, and preferably within reference marks 31b so long as proper body posture is maintained, as a result of the continuous bouncing motion of the individual 12 while walking or running.

Figure 2:
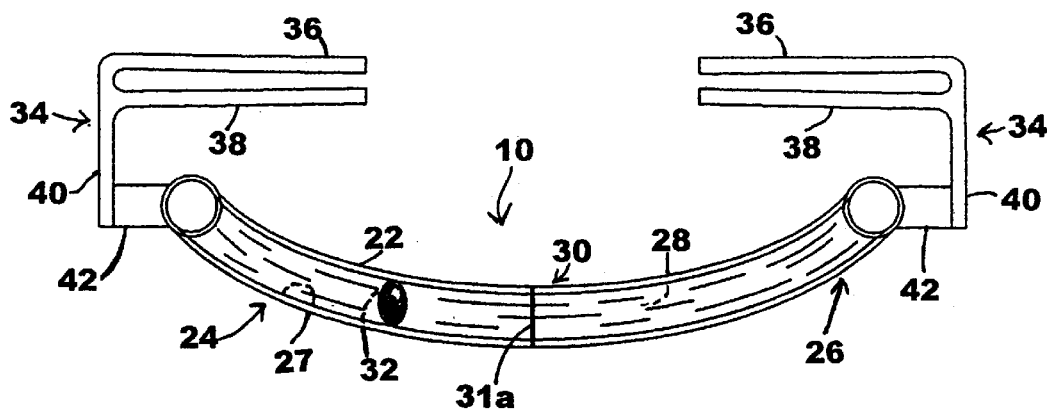
FIG. 2 is an enlarged front elevational view of the device first shown in FIG. 1.

In its preferred embodiment, the shiftable means can be a spherical member, and a preferable spherical member is shown in FIGS. 1, 2, and 5. The spherical member illustrated in FIGS. 1, 2, and 5 is a ball bearing 32 having a diameter less than the inside diameter of the bore 28 to allow the ball bearing 32 to roll freely within the bore 28. Other alternative embodiments for the shiftable means can be a marble, a pellet, or a BB, and such spherical members can be colored to suit the purchaser or coated with a fluorescent material for safety purposes and for providing an additional nighttime visibility element to the device 10. In addition, the bore 28 can be almost completely filled with a liquid and then closed off whereupon a single gas bubble can be trapped within the fluid for entrainment within the region within reference marks 31b. In operation, the gas bubble would move within the bore 28 as a result of the lateral movement of the individual 12 for registering deviations from proper body posture. Also, the bottom inside or outside of the sidewall 27 of the tube 22 could be coated with a reflective substance to reflect the air bubble that would be located against the top inside surface of the sidewall of the tube 22. Moreover, if the shiftable means is a spherical member, the spherical member can be coated or painted with a fluorescent material so it would be viewable at nighttime, thereby allowing the individual 12 to monitor his performance and posture during nighttime walks or runs. Also, the spherical member could be coated with a substance that would emit, or be receptive to, thermal radiation, such as infrared radiation.

Shown in FIGS. 1–6 are several embodiments of a removable securement or fastening means for attaching the tube 22 to the bill 14 of the cap 16 and also for closing off the bore 28 at ends 24 and 26. Specifically, illustrated in FIGS. 1–5 is a fastening means that comprises a clip 34 that can be easily slipped onto the bill 14 and quickly removed therefrom. The clip 34 includes an upper gripping member or jaw 36 spaced from a lower gripping member or jaw 38. Both jaws 36 and 38 are slightly flexible so that they can slip onto the upper and lower surfaces of the bill 14. Both jaws 36 and 38 are integrally attached to a generally triangular-shaped bridging portion 40 which extends perpendicular to the orientation of the jaws 36 and 38. Spaced from the jaws 36 and 38, but projecting parallel therewith, is a cylindrical receiving or insertion barrel 42 that includes an interior splined bore 44. The bore 44 includes three longitudinally-extending, triangular-shaped, adjacent recesses or slots 46 that are coequal in length with the barrel 42 and bore 44. In addition, the clip 34 of FIGS. 1–5 includes an intermediate connection member 48 which actually attaches the ends 24 and 26 of the tube 22 to each respective clip 34. The connection member 48 includes a cylindrical-shaped plug 50 which is removably insertable into the first end 24 and second end 26. Integrally attached to the plug 50, and extending at a right angle thereto, is an elongated, cylindrical splined shaft 52 having a single projection or tooth 54 extending along the length of the shaft 52. Projecting outward from the shaft 52, and coaxial therewith, is a stem 56 which is of a smaller diameter than the shaft 52. Mounted at the end of the stem 56 is a slightly deformable ball or stopper 58. One method of assembling the clips 34 to the tube 22 would be for the individual 12 to insert each plug 50 into the bore 28 at the respective ends 24 and 26. The individual 12 would then slide the barrel 42 onto the shaft 52 so that the tooth 54 initially mates with one of the three recesses 46 formed in the barrel 42. The stopper 58 will have a diameter that is slightly larger than the bore 44. The stopper 5 is slightly deformable and, thus, upon insertion, the stopper 58 will slightly expand and become wedged within the bore 44. This prevents shaft 52 from sliding out of the bore 44 which would cause the tube 22 to become detached from the clip 34. When both clips 34 have been assembled in the above-described manner, the jaws 36 and 38 can be slid or slipped over the upper and lower surfaces of the bill 14 adjacent the area where the bill 14 attaches to the cap 16. With the jaws 36 and 38 secured to the opposed sides of the bill 14, the device 10 is now mounted to the cap 16 in the use position.

Some adjustment of the position of the tube 22 with respect to the eye level of the individual 12 may be necessary. In order to adjust the disposition of the tube 22 so that the spherical member, such as the ball bearing 32, is viewable by the individual 12 at or near eye level, the individual 12 simply grasps each connection member 48 and the tube 22 and then pivots or rotates the shaft 52 inserted within the barrel 42 so that the tooth 54 mates with the appropriate one of the three longitudinal recesses 46 formed in the bore 44. The tube 22 can be pivoted upward or downward until the individual 12 attains the appropriate disposition for viewing the ball bearing 32. Generally, three recesses 46 are all that are necessary for obtaining maximum adjustment of the tube 22.

Figure 6:
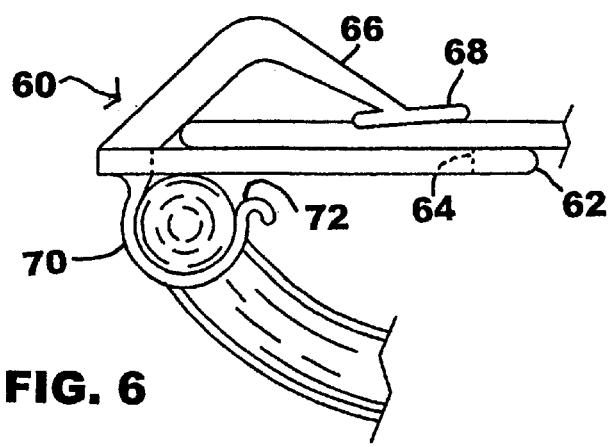
FIG. 6 is a perspective view of an alternative embodiment of a fastening element for attaching the device first shown in FIG. 1 to the bill of a cap.

Illustrated in FIG. 6 is an alternative embodiment for a removable securement or fastening means for the device 10. The removable fastening means of FIG. 6 comprises a pair of semi-flexible, removably attachable clips 60 (only one is shown) which are easily and quickly secured to, and removed from, the bill 14 and the tube 22. The clip 60 includes a main plate 62 having a rectangular shape and an elongated slot 64 extending almost the length of the plate 62. A manually-depressible arm 66 is attached to one end of the plate 62 and extends upwardly from the plate 62 and also includes a portion capable of projecting downwardly through the slot 64. The distal end of the arm 66 includes a first manually-operable gripping member, foot, or clamp 68 which, in its non-disposed stated, is spaced from the upper surface of the plate 62. In order to move the clamp 68 away from the plate 62, the arm 66 is manually lifted up a slight distance so that a gap is formed between plate 62 and clamp 68. Integrally attached to the underside of the plate 62, and extending opposite the arm 66, is a flexible, circular-shaped second manually-operable hook, snap, or clamp 70 which defines a receiving aperture 72.

In order to attach the tube 22 to the bill 14 using clips 60, the individual 12 can first attach the opposite ends 24 and 26 to each respective clamp 70 by manually and slightly lifting the clamps 70 so that the ends 24 and 26 can be snapped or clamped within the respective aperture 72 whereupon at least approximately one inch of the tube 22 at each end 24 and 26 should project through the respective aperture 72. In order to attach clips 60 to opposite sides of the bill 14, the individual 12 would position the tube 22 with the clips 60 attached thereto at a position level with the opposite sides of the bill 14 adjacent the point where the bill 14 merges with the cap 16. The individual 12 would then lift up arm 68 and then slide both clips inward on the upper and lower surfaces of the bill 14 so that plate 62 slides on the lower surface of the bill 14 and clamp 68 slides on the upper surface of the bill 14. The individual 12 would then slide both clips 60 inward until the bill 14 abuts the inner portion of the arm 66 adjacent the point where the arm 66 attaches to the plate 62. Clips 60 can be further adjusted by sliding the clips 60 along the outer peripheral edge of the bill 14 either rearward toward the cap 16 or forward to the forward midpoint of the bill 14 so that optimal viewing of the spherical member, such as ball bearing 32, can be obtained. Both clips 34 and 60 can be coated with a fluorescent material or can have reflective coatings or strips applied thereto for providing additional safety for nighttime workout or training sessions. Also, both clips 34 and 60 could be fitted with lights, such as battery operated miniature lights.

Although a certain preferred embodiment has been shown and described in detail, it should be understood that various changes and modifications may be made therein without departing from the scope of the appended claims.

What is claimed is:

1. A runner's headgear disposed on a runner's head and having a bill with an arcuate outer edge projecting forward from the runner's forehead and above eye level;

an elongated tube having a constant diameter and being removably attached on the underside of the bill and arcuately shaped whereby it is disposed in parallel subjacency to the bill's outer edge;

the tube having a central transparent section;

a spherical member contained within the tube and having a diameter less than the inside diameter of the tube whereby the spherical member can shift within the tube;

clamp means at each end of the tube for removably attaching the tube end to the bill;

each clamp means having a ring-like portion tightly encircling the tube end;

a manually releasable clamp section formed integral to the ring portion;

the clamp section having a rigid body portion and an opposed elastically deformable finger portion for firmly removably gripping the bill; and markings on the tube defining a central tube area visually apparent to the runner and serving as a concentration point in the runner's field of vision.

2. The runner's headgear of claim 1 wherein the clamp means is rigid plastic and has a plug portion fitted tightly within the tube end and a pair of spaced-apart parallel jaws for slidably fitting onto the headgear bill.

* * * * *